United States Patent [19]

Goldman et al.

[11] Patent Number: 4,550,164

[45] Date of Patent: Oct. 29, 1985

[54] PROCESS FOR PREPARING 2-METHYL-2-HYDROXYPROPYL PIPERAZINE-1-CARBOXYLATE COMPOUNDS

[75] Inventors: Irving M. Goldman, Niantic; Donald E. Kuhla, Ledyard; Constantine Sklavounos, Waterford, all of Conn.

[73] Assignee: Pfizer Inc., New York, N.Y.

[21] Appl. No.: 257,365

[22] Filed: Apr. 24, 1981

Related U.S. Application Data

[63] Continuation of Ser. No. 81,226, Oct. 2, 1979, abandoned, which is a continuation-in-part of Ser. No. 907,082, May 18, 1978, abandoned.

[51] Int. Cl.[4] .......................................... C07D 403/04
[52] U.S. Cl. .................................... 544/291; 544/389
[58] Field of Search ................................ 544/389, 291

[56] References Cited

U.S. PATENT DOCUMENTS 3,703,538 11/1972 Mulheimmer et al. ......... 260/482 C
3,935,213 1/1976 Hess .................................... 544/389

FOREIGN PATENT DOCUMENTS 1249852 9/1967 Fed. Rep. of Germany .
0062617 2/1955 France .
1096204 6/1955 France .

OTHER PUBLICATIONS

Lucas, *Organic Chemistry*, 2nd ed. 1953, Amer. Book Co., New York, p. 376.
Katzhendler et al., "Journ. Chem. Soc.", Perkins Trans., vol. 2, 1972, pp. 2019–2025.
Baizer et al., "J. Org. Chem.", vol. 22, 1972, p. 1706.

*Primary Examiner*—Richard L. Raymond
*Assistant Examiner*—James H. Turnipseed
*Attorney, Agent, or Firm*—Connolly and Hutz

[57] ABSTRACT

Isobutylene carbonate and certain 1-substituted piperazine compounds are reacted in a process that forms 2-methyl-2-hydroxypropyl 4-substituted piperazine-1-carboxylate compounds which are medicinal agents or synthetic intermediates for such agents. The features of the process allow the preparation of an essentially pure 2-methyl-2-hydroxypropyl carboxylate compound.

10 Claims, No Drawings

PROCESS FOR PREPARING 2-METHYL-2-HYDROXYPROPYL PIPERAZINE-1-CARBOXYLATE COMPOUNDS

CROSS REFERENCE TO RELATED APPLICATIONS

This is a continuation of application Ser. No. 81,226 filed Oct. 2, 1979, now abandoned, which in turn is a continuation-in-part of application Ser. No. 907,082 filed May 18, 1978, now abandoned.

BACKGROUND

The invention relates to an improved process for preparing the 2-methyl-2-hydroxypropyl piperazine-1-carboxylate moiety of certain preferred quinazoline derivatives which are useful antihypertensive agents. In general this moiety is a member of a large class of 2-position substituents of quinazoline antihypertensive agents which are described in the following U.S. Pat. Nos.: 3,980,650, 3,935,213, 3,769,286, 3,669,968, 3,663,706, 3,635,979 and 3,511,836. In particular the quinazoline agents possessing this moiety are mentioned in the '286, '968 and '706 patents as being especially interesting because they have a high degree of hypotensive activity.

Known synthetic procedures for forming the preferred quinazoline derivatives such as 2-methyl-2-hydroxypropyl 4-(4-amino-6,7,8-trimethoxyquinazolin-2-yl)piperazine-1-carboxylate or its corresponding 6,7-dimethoxy analog all employ hydration of a methallyl carbonate moiety to form the desired 2-methyl-2-hydroxy-propyl group (U.S. Pat. Nos. 3,663,706 and 3,769,286). Several synthetic variations of this route are described but no matter which is used, the yield of the 2-methyl-2-hydroxypropyl piperazine-1-carboxylate moiety is low owing to competing hydrolysis of the carbamate group during hydration of the methallyl group.

Another method for synthesis of this type of moiety employs the reaction of carbonates with amines to form the corresponding carbamates. The reaction has been extensively studied and the variety of carbonates and amines used is illustrated by the following: J. Katzhendler et. al., *J. Chem. Soc., Perkin Trans.* 2, 1972, 2019; U.S. Pat. No. 3,703,538; M. Baizer et. al., *J. Org. Chem.*, 22, 1706 (1957); French Pat. No. 1,096,204 and French Patent of Addition 62617.

According to the carbonate method, isobutylene carbonate is required for the synthesis of the 2-methyl-2-hydroxypropyl piperazine-1-carboxylate side chain. However, its reaction with amine is capable of producing two isomers. Hence it would not be expected to provide an effective route to the desired antihypertensive agents because of significant contamination with the unwanted structural isomer.

A confusing story is presented by the prior art. According to the French addition patent, the reaction of a similar asymmetric carbonate, propylene carbonate, with amines in water produces the 2-hydroxyprop-1-yl carbamate compound rather than the 1-hydroxyprop-2-yl structural isomer. These results are refuted by Beizer and Katzhendler who show that mixtures of the two possible isomers are obtained.

It is thus surprising to discover that the desired 2-methyl-2-hydroxypropyl piperazine-1-carboxylate compound is produced essentially free of the undesired structural isomer when isobutylene carbonate is reacted with the appropriate piperazine compound according to the processes of the present invention.

SUMMARY

According to the present invention a 2-methyl-2-hydroxypropyl 4-substituted-piperazine-1-carboxylate compound of the structure

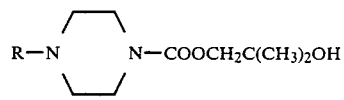

wherein R is hydrogen, cyano, 4-amino-6,7,8-trimethoxyquinazolin-2-yl or 4-amino-6,7-dimethoxyquinazolin-2-yl, is synthesized by reacting isobutylene carbonate with a piperazine compound of the formula

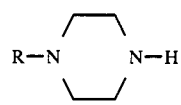

Under the reaction conditions of the invention a gross, kinetic mixture of the desired 2-methyl-2-hydroxypropyl carboxylate compound and the corresponding 1,1-dimethyl-2-hydroxyethyl 4-substituted piperazine-1-carboxylate structural isomer is initially formed but is converted into essentially pure carboxylate compound. This synthetically useful conversion means that the carboxylate compound is available for drug use with little or no other purification. The structural isomer does not have to be removed by expensive, time consuming purification procedures such as chromatography. Therefore in this context the carboxylate compound is considered essentially pure or essentially free of the unwanted structural isomer when the ratio of carboxylate compound to structural isomer is at least 95 to 5. In actual practice the reaction is usually continued until there is no detectable amount of the structural isomer.

The conditions of the reaction process are as follows. If the piperazine compound and isobutylene carbonate are reacted without solvent, a neat melt is used covering temperatures from one at which the isobutylene carbonate and piperazine compound are in the liquid state to one about at which the isobutylene carbonate or piperazine compound refluxes or decomposes. Although the actual temperature required to produce the liquid state will vary somewhat with the identity of the piperazine compound, a temperature range of about 65° to about 185° or reflux will usually produce the liquid state and avoid decomposition. If the piperazine compound and isobutylene are reacted in a polar, protic solvent, the temperature must be within the range of from ambient to reflux. If the piperazine compound and isobutylene carbonate are reacted in a polar or nonpolar, aprotic solvent, the temperature must be at least about 70° to reflux.

Some appropriate polar, protic solvents are water, methanol and ethanol. Some polar or nonpolar, aprotic solvents are acetonitrile, dimethylformamide, diethylformamide, dimethylacetamide, diphenyl ether, bis(2-methoxyethyl)ether, benzene and mono-, di-, and trimethyl benzene.

The invention also includes two other methods for preparing the 2-methyl-2-hydroxypropyl carboxylate compound. The first method involves rearrangement of the 1,1-dimethyl-2-hydroxyethyl 4-substituted-piperazine-1-carboxylate structural isomer. According to this method, the structural isomer or a gross mixture of it and the 2-methyl-2-hydroxypropyl carboxylate compound is maintained at a temperature of at least about 70° C. in a polar or nonpolar, aprotic solvent or at ambient to reflux temperature in polar, protic solvent until essentially pure carboxylate compound is produced.

The second method involves only the preparation of 2-methyl-2-hydroxypropyl piperazine-1-carboxylate. When isobutylene carbonate and piperazine are combined, a competing side reaction can form the bis adduct. It is usually avoided by using excess piperazine but any undesired bis adduct contaminant may be converted to the desired carboxylate compound by refluxing in excess piperazine. Thus bis-(2-methyl-2-hydroxypropyl)piperazine-1,4-dicarboxylate, 2-methyl-2-hydroxypropyl-1',1'-dimethyl-2'-hydroxyethyl piperazine-1,4-dicarboxylate, bis(1,1-dimethyl-2-hydroxyethyl)piperazine-1,4-dicarboxylate, any combination thereof or any mixture with the desired carboxylate compound or the structural isomer may be converted to the desired carboxylate compound by reflux in excess piperazine.

DETAILED DESCRIPTION

According to the present invention the following reaction is conducted to form a 2-methyl-2-hydroxypropyl carboxylate compound wherein R is as defined above.

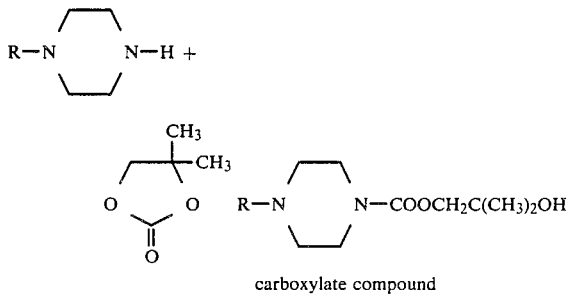

carboxylate compound

Additionally the 1,1-dimethyl-2-hydroxyethyl 4-substituted-piperazine-1-carboxylate structural isomer or a gross mixture of it and the 2-methyl-2-hydroxypropyl carboxylate compound, either of which have been prepared by any known method may be converted to essentially pure carboxylate compound by using the reaction conditions of the invention.

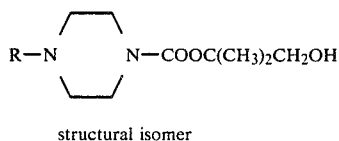

structural isomer

The important features of the process are as follows. If the piperazine compound and isobutylene carbonate are reacted in a polar, protic solvent such as water, methanol, ethanol and the like, the temperature must be in the range of ambient to reflux. If the piperazine compound and isobutylene carbonate are reacted in polar or nonpolar, aprotic solvent, the temperature must be at least about 70° C. to reflux. Suitable polar or nonpolar aprotic solvents are acetonitrile, dimethylformamide, diethylformamide, dimethylacetamide, diphenyl ether bis-2-(methoxyethyl)ether, benzene, mono-, di- and tri-methyl benzene and the like. If the piperazine compound and isobutylene carbonate are reacted in undiluted form, without solvent, a neat melt is used covering temperatures cover the range from the point at which the isobutylene carbonate and piperazine compound are in the liquid state to the point about which the isobutylene carbonate or piperazine compound refluxes or decomposes. In usual practice the neat melt reaction will be run at temperatures from about 65° to about 185° or reflux which will be sufficient to put the reaction in the liquid state.

The time required to produce the desired essentially pure carboxylate compound depends upon the type of solvent and temperatures used. In general enough time must be allowed to establish thermodynamic equilibrium. Therefore it is common to monitor the increase in concentration of the desired carboxylate compound relative to the structural isomer and stop the reaction when there is no further increase. In common practice about 30 min. to about 240 min. will be sufficient to produce essentially pure carboxylate compound.

The sequence of mixing of the starting materials in the neat reaction or the solution reaction is unimportant. They both may be present in the reaction pot before it is heated or the amine may be heated to the appropriate reaction temperature and then the isobutylene carbonate may be added.

To transform the bis adduct of piperazine and isobutylene carbonate into the desired carboxylate compound, any mixture containing the bis adduct or the isolated bis adduct itself may be refluxed in piperazine while monitoring the production of the carboxylate compound. Furthermore whenever there is a possibility of carbonate reaction at both amine positions of the piperazine compound, the bis adduct competing side reaction can be minimized or avoided by using excess piperazine compound. It is usual practice to use about a 2 to 3 molar equivalent excess.

The progress of the reaction can be monitored by any sampling technique that will establish the relative concentrations of the carboxylate compound and the structural isomer. For example the ratio of the 2-methyl-2-hydroxypropyl carboxylate compound to the 1,1-dimethyl-2-hydroxyethyl structural isomer can be determined by comparing respective NMR absorptions of the gem dimethyl groups. Other techniques such as high pressure liquid chromatography, thin layer chromatography and gas chromatography may also be used to establish the relative amounts of the two isomers. The reaction may be considered to have reached thermodynamic equilibrium when the carboxylate compound is shown by such an analysis to be essentially free of the structural isomer, i.e., when the ratio of carboxylate compound to structural isomer is at least 95 to 5. In usual practice there will be no detectable structural isomer.

Isolation of the desired carboxylate compound can be accomplished by the usual methods. For example, partitioning the reaction mixture between aqueous and organic layers, the aqueous layer being acidified if appropriate, and taking the necessary steps to isolate the residue from the selected partition layer followed by recrystallization of the residue will surffice. Another method involves crystallizing the desired carboxylate compound directly from the nonpolar, aprotic solvent used in the reaction.

The compounds prepared by the process of the invention are substituted quinazoline medicinal agents or are intermediates which are transformed to the medicinal agents by known methods as described above. The process allows the preparation of the intermediates or the agents in high yields using inexpensive, non-toxic starting materials and does not rely upon phosgene.

Examples 1 through 6 show that the process of the invention achieves the synthesis of the desired 2-methyl-2-hydroxypropyl carboxylate compound which is essentially free of the structural isomer. NMR analysis indicates that a gross mixture of the two isomers is kinetically formed but as the process continues the desired carboxylate compound is thermodynamically produced in an essentially pure state.

The following examples are merely illustrative and in no way limit the scope of the appended claims. The IR spectral data were obtained on a diffraction grading infrared spectrometer and are given in cm$^{-1}$. The NMR spectral data were obtained on a Varian T-60 spectrometer and are given in delta ppm. In general the temperatures of the reactions described in the Examples are bath temperatures and are uncorrected. When the temperature is unspecified, it will be taken to mean ambient or room temperature which varies from 15° to 30° C.

The progress of the reactions described in the examples were determined by monitoring with NMR spectroscopy. Aliquots were taken, cooled and measured to ascertain the relative ratios of the isomers. In the alternative the reaction was conducted for a given length of time and cooled, followed by analysis by NMR spectroscopy.

When the ratio of carboxylate compound to structural isomer is not indicated in the following examples, it will be taken to mean that no structural isomer has been detected with the analytical methods used.

Preparation A 2-(1-piperazinyl)-4-amino-6,7,8-trimethoxyquinazoline(11)

A solution of 28.1 g (32.6 mmoles) of anhydrous piperazine in 600 ml iso-amyl alcohol was refluxed for 96 hours via a soxhlet extraction apparatus charged with 8.78 g (32.6 mmoles) of 2-chloro-4-amino-6,7,8-trimethoxyquinazoline. The reaction mixture was condensed in vacuo to a dark residue and then partitioned between water and chloroform. The chloroform layer was dried (Na$_2$SO$_4$) and evaporated in vacuo to dryness. The gummy residue was treated with ethanolic hydrogen chloride and the precipitated hydrochloride of the title compound (11) was recrystallized from chloroform/methanol/isopropyl ether: m.p. 236°–239°. The free base title compound (11) was obtained from the hydrochloride by the standard usual procedures and recrystallized from methanol/ethyl acetate, m.p. 201°–3° C.

EXAMPLE 1

Preparation of 2-Hydroxy-2-methylpropyl piperazine-1-carboxylate (1)

To 66.7 g (0.776 mole) of refluxing piperazine was dropwise added within 10 minutes, 30 g (0.258 mole) of isobutylene carbonate. The mixture was refluxed for 45 minutes and then allowed to cool to room temperature. The resulting thick oil was dissolved in 110 ml methylene chloride and an amount of 6N hydrochloric acid sufficient to adjust the pH to 2.8 was added while maintaining the temperature of the stirred mixture below 10° C. The aqueous layer was separated, mixed with 400 ml of chloroform and an amount of 6N sodium hydroxide sufficient to adjust the pH to 9.9 was added while maintaining the temperature of the mixture below 5° C. The aqueous layer was re-extracted with 300 ml chloroform, the combined chloroform layers were dried (MgSO$_4$), and the solvent evaporated in vacuo. The residue was purified by crystallization from methylisobutyl-ketone-hexanes to give 32.8 g (63%) of the title compound (1) as a white crystalline solid: m.p. 77–79; NMR (CDCl$_3$) δ 1.23 (s, 6, gem (CH$_3$)), δ 2.8 (m, 4, piperazine protons), δ 3.43 (m, 4, piperazine protons), and δ 3.93 ppm (s, 2, CH$_2$).

EXAMPLE 2

Time study of conversion of 1,1-dimethyl-2-hydroxyethyl piperazine-1-carboxylate (2) to 2-hydroxy-2-methyl propyl piperazine-1-carboxylate (1)

To 375 mg (4.36 mmole) of piperazine at 120° C. was added 253.4 mg (2.18 mmole) of isobutylene carbonate. The mixture was maintained at 120° C. and samples were periodically removed, cooled and analyzed by NMR spectroscopy (CDCl$_3$) to ascertain the presence and/or amount of (a) isobutylene carbonate; (b) tertiary alcohol, compound (1); and (c) primary alcohol, compound (2). According to the analysis, the absence at the 2 minute interval of the 1.55 ppm gem dimethyl absorption of isobutylene carbonate indicated that it had completely reacted. The dynamic ratio of the yield of the tertiary (1) to primary (2) alcohol with respect to time was estimated from the relative intensities of the NMR absorptions of the gem dimethyl groups of the tertiary alcohol (δ 1.23 ppm) and the primary alcohol (δ 1.38 ppm). The relation is shown below.

| time (min) | tertiary/primary alcohol |
| --- | --- |
| 2 | approximately 50/50 |
| 15 | 73/27 |
| 30 | 88/12 |
| 45 | 93/7 |
| 60 | 96/4 |

EXAMPLE 3

Preparation of 2-hydroxy-2-methylpropyl 4-cyanopiperazine-1-carboxylate (3)

To 1.11 g (10 mmoles) of 1-cyanopiperazine at 150° C. was added 1.16 g (10 mmoles) of isobutylene carbonate. The stirred mixture was maintained at 120° C. for 20 hours and then allowed to cool to room temperature. The title compound (3) crystallized on standing: m.p. 90°–92° C.; NMR (CDCl$_3$) δ 1.23 (s, 6, gem CH$_3$), δ 3.25 (m, 4, piperazine protons), δ 3.58 (m, 4, piperazine protons), and δ 3.95 ppm (s, 2, CH$_2$); IR (neat) 3450, 2975, 2225 (C≡N), and 1700 cm$^{-1}$ (C=O).

EXAMPLE 4

Preparation of 2-hydroxy-2-methylpropyl 4-(4-amino-6,7,8-trimethoxy-2-quinazolin-2-yl)piperazine-1-carboxylate (4)

A stirred mixture of 2.32 g (20 mmoles) of isobutylene carbonate and 1.59 g (5 mmoles) of 2-(1-piperazinyl)-4-amino-6,7,8-trimethoxy quinazoline (11) was heated at 180° C. for 5 hours. After cooling, the reaction mixture was partitioned between water and methylene chloride, the organic layer separated and dried ($MgSO_4$), and the solvent removed in vacuo. The residue was dissolved in ethyl acetate and the resulting solution was condensed to a small volume and cooled to crystallize the title compound (4). The identity of the title compound (4) was confirmed by comparison of its IR and NMR spectra with those of authentic material.

EXAMPLE 5

Preparation of 2-hydroxy-2-methylpropyl 4-(4-amino-6,7-dimethoxy-2-quinazolin-2-yl)piperazine-1-carboxylate (5)

A stirred solution of 580 mg (5 mmoles) of isobutylene carbonate and 54 mg (0.186 mmole) of 1-(4-amino-6,7-dimethoxy-2-quinazolinyl)piperazine was heated at 185° C. for 18 hours. After cooling to room temperature the reaction mixture was analyzed by HPLC comparison to authentic material and found to contain the title compound (5).

EXAMPLE 6

Preparation of carboxylate compound (1) using a nonpolar, aprotic reaction solvent A mixture of 60.0 g (0.516 mole) of isobutylene carbonate, 133.0 g (1.519 mole) of piperazine, and 500 ml of toluene was refluxed for 22 hours and then cooled to room temperature whereupon piperazine separated and was removed by filtration. After atmospheric co-distillation of a mixture of additional excess piperazine and the solvent, the solution was cooled to crystallize the title compound (1). The yield was 84.0 g (80%); m.p. 78°–80° C.

EXAMPLE 7

Preparation of carboxylate compound (1) using water as a reaction solvent.

To a solution of 1.74 g (20 mmole) of piperazine in 2.0 ml of water was added 0.58 g (5 mmole) isobutylene carbonate. The resulting solution was stirred at room temperature for 45 minutes, saturated with sodium chloride, and extracted with 20 ml of methylene chloride. The organic layer was dried ($MgSO_4$), and the title compound (1) was crystallized by the addition of toluene to give a 75% yield.

EXAMPLE 8

Time study of the conversion of structural isomer (2) to carboxylate compound (1) in $D_2O$ To a solution of 174 mg (2 mmole) of piperazine in 1 ml of deuterium oxide was added 58 mg (0.5 mmole) of isobutylene carbonate. The mixture was analyzed periodically by NMR spectroscopy to ascertain the presence and concentration of (a) isobutylene carbonate; (b) tertiary alcohol, compound (1); (c) primary alcohol, compound (2); and (d) isobutylene glycol, the hydrolysis product of isobutylene carbonate. The relative abundance of these compounds in the mixture was estimated from the intensities of the NMR absorptions of the gem dimethyl groups. The results of the analyses as well as the NMR shifts of the gem dimethyl absorption are shown below.

| Time (min) | Compound (1) $\delta 1.23$ ppm | Compound (2) ($\delta 1.38$ ppm) | Isobutylene carbonate ($\delta 1.50$ ppm) | Isobutylene glycol ($\delta 1.18$ ppm) |
|---|---|---|---|---|
| 10 | 62.5 | 12.9 | 10.9 | 13.6 |
| 17 | 73.4 | 8.2 | 4.8 | 13.5 |
| 24 | 78.9 | 3.7 | 1.8 | 15.5 |
| 31 | 80.7 | 1.8 | 0.9 | 16.5 |
| 38 | 82.6 | 0.8 | 0.0 | 16.5 |

EXAMPLE 9

Time study of the conversion of structural isomer (2) to carboxylate compound (1) in $CH_3OD$ To a solution of 174 mg (2 mmole) of piperazine in 1 ml of deuterated methyl alcohol was added 58 mg (0.5 mmole) of isobutylene carbonate. The mixture was analyzed periodically as in Example 8. The results of the analysis are shown below.

| Time (hrs) | Compound (1) ($\delta 1.20$ ppm) | Compound (2) ($\delta 1.40$ ppm) | Isobutylene carbonate ($\delta 1.50$ ppm) |
|---|---|---|---|
| 0.25 | 22.1 | 22.1 | 54.7 |
| 0.75 | 34.4 | 35.0 | 30.6 |
| 1.33 | 39.8 | 40.0 | 20.2 |
| 1.83 | 43.0 | 42.0 | 15.0 |
| 17.17 | 68.9 | 28.6 | 2.4 |
| 24.25 | 74.8 | 23.6 | 1.6 |
| 41.67 | 82.9 | 15.5 | 1.5 |
| 65.50 | 92.1 | 7.9 | 0.0 |
| 100.00 | 96.5 | 3.5 | 0.0 |

EXAMPLE 10

Preparation of carboxylate compound (1) using acetonitrile as a reaction solvent To a solution of 174 mg (2 mmole) of piperazine in 1 ml of acetonitrile maintained at 70° C. was added 58 mg (0.5 mmole) of isobutylene carbonate. The resulting solution was stirred at the above temperature for 150 hours following which the solvent was removed in vacuo. The residue was analyzed by NMR spectroscopy as in Example 3. According to the analysis, isobutylene carbonate had completely reacted and compound (1) and compound (2) were present in 95 to 5 molar ratio.

EXAMPLE 11

Demonstration that an elevated temperature must be used with polar or nonpolar aprotic solvents for the preparation of carboxylate compound (1)

To a solution of 1.74 g (0.02 mole) of piperazine in 20 ml of acetonitrile was added 0.58 g (0.005 mole) isobutylene carbonate. The resulting solution was stirred at room temperature for 168 hours following which the solvent was removed in vacuo. The residue was analyzed by NMR spectroscopy ($CDCl_3$) as in Example 3.

According to the analysis, structural isomer (2) and carboxylate compound (1) were present in a 3 to 1 molar ratio but isobutylene carbonate was absent. The mixture was then dissolved in 20 ml water and the solution was stirred for 30 minutes to produce (1) to (2) in a ratio of 95 to 5. The solution was then saturated with sodium chloride and extracted with 20 ml of methylene chloride. The organic layer was separated, dried (MgSO4), and the title compound (1) was crystallized by the addition of toluene to give a 75% yield.

EXAMPLE 12

Preparation of carboxylate compound (1) from bis-2-hydroxy-2-methylpropyl piperazine-1,4-dicarboxylate and piperazine To 1.72 g (20 mmole) of refluxing piperazine was added 0.636 g (2 mmole) of bis-2-hydroxy-2-methylpropyl piperazine-1,4-dicarboxylate. The mixture was refluxed for 45 minutes and then allowed to cool to room temperature. The resulted solid was analyzed by GC comparison to authentic material and found to contain 375 mg (92.8%) of title compound (1) which was recovered by the isolation procedure of Example 1.

We claim:

1. A process for preparing a 2-methyl-2-hydroxypropyl-4-substituted piperazine-1-carboxylate compound of the structure

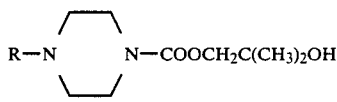

wherein R is selected from the group consisting of hydrogen, cyano, 4-amino-6,7,8-trimethoxyquinazolin-2-yl and 4-amino-6,7-dimethoxyquinazolin-2-yl, which comprises:

reacting a piperazine compound of the structure

with isobutylene carbonate in or without solvent until thermodynamic equilibrium is established, whereby the 2-methyl-2-hydroxypropyl carboxylate compound is produced essentially free of the corresponding 1,1-dimethyl-2-hydroxyethyl 4-substituted piperazine-1-carboxylate structural isomer, provided that when the piperazine compound and isobutylene carbonate are reacted without solvent, a neat melt is used covering temperatures from one at which the piperazine compound and isobutylene carbonate are in the liquid state to one at which the piperazine compound or isobutylene carbonate refluxes or decomposes, when the piperazine compound and isobutylene carbonate are reacted in a polar, protic solvent the temperature is within the range of ambient to reflux, and when the piperazine compound and isobutylene carbonate are reacted in a polar or nonpolar, aprotic solvent, the temperature is at least 70° C. to reflux.

2. A process of claim 1 wherein the reaction is conducted in a polar, protic solvent selected from water, methanol or ethanol.

3. A process of claim 1 wherein the reaction is conducted in a polar or nonpolar, aprotic solvent selected from acetonitrile, dimethylformamide, diethylformamide, dimethylacetamide, diphenyl ether, bis(2-methoxyethyl)ether, benzene and mono-, di- and trimethylbenzene.

4. A process of claim 1 wherein the piperazine compound and isobutylene carbonate are reacted as a neat melt at temperatures from about 65° to about 185°.

5. A process of claim 1 wherein the 2-methyl-2-hydroxypropyl carboxylate compound to be prepared is 2-methyl-2-hydroxypropyl piperazine-1-carboxylate.

6. A process of claim 5 wherein 2 to 3 molar equivalents of piperazine per molar equivalent of isobutylene carbonate is used.

7. A process of claim 5 which further comprises isolating the 2-methyl-2-hydroxypropyl piperazine-1-carboxylate in pure form by crystallizing it directly from the reaction mixture containing a polar or nonpolar, aprotic solvent.

8. A process of claim 1 wherein the 2-methyl-2-hydroxypropyl carboxylate compound to be prepared is 2-methyl-2-hydroxypropyl 4-(4-amino-6,7,8-trimethoxyquinazolin-2-yl)piperazine-1-carboxylate.

9. A process ofr preparing a 2-methyl-2-hydroxypropyl 4-substituted piperazine-1-carboxylate compound of the structure

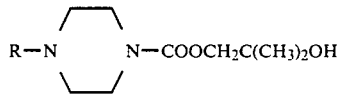

wherein R is selected from the group consisting of hydrogen, cyano, 4-amino-6,7,8-trimethoxyquinazoline-2-yl and 4-amino-6,7-dimethoxyquinazoline-2-yl, which comprises:

maintaining the corresponding 1,1-dimethyl-2-hydroxyethyl 4-substituted piperazine-1-carboxylate structural isomer or a gross mixture of it and the 2-methyl-2-hydroxypropyl carboxylate compound at a temperature of at least about 70° C. in a polar or nonpolar aprotic solvent or at ambient temperature in polar, protic solvent until the essentially pure 2-methyl-2-hydroxypropyl carboxylate compound is produced.

10. A process for preparing essentially pure 2-methyl-2-hydroxypropyl piperazine-1-carboxylate, which comprises refluxing a mixture of excess piperazine and bis-(2-methyl-2-hydroxypropyl)piperazine-1,4-dicarboxylate, 2-methyl-2-hydroxypropyl-1′,1′-dimethyl-2′-hydroxyethyl piperazine-1,4-dicarboxylate or bis-1,1-dimethyl-2-hydroxyethyl piperazine-1,4-dicarboxylate or combination thereof or any mixture thereof with 2-methyl-2-hydroxypropyl piperazine-1-carboxylate or 1,1-dimethyl-2-hydroxypropyl piperazine-1-carboxylate.

* * * * *